United States Patent
Annis et al.

(10) Patent No.: US 9,521,849 B2
(45) Date of Patent: *Dec. 20, 2016

(54) BIOCIDAL COMPOSITION OF 2,6-DIMETHYL-M-DIOXANE-4-OL ACETATE AND METHODS OF USE

(71) Applicant: Dow Global Technologies Inc., Midland, MI (US)

(72) Inventors: Ioana Annis, Mundelein, IL (US); Jon B. Raymond, Buffalo Grove, IL (US); Emerentiana Sianawati, Vernon Hills, IL (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 99 days.

This patent is subject to a terminal disclaimer.

(21) Appl. No.: 14/287,522

(22) Filed: May 27, 2014

(65) Prior Publication Data

US 2014/0256777 A1 Sep. 11, 2014

Related U.S. Application Data

(62) Division of application No. 12/619,715, filed on Nov. 17, 2009, now Pat. No. 8,765,806.

(60) Provisional application No. 61/116,303, filed on Nov. 20, 2008.

(51) Int. Cl.
*A01N 43/80* (2006.01)
*A01N 43/32* (2006.01)

(52) U.S. Cl.
CPC ............... *A01N 43/80* (2013.01); *A01N 43/32* (2013.01)

(58) Field of Classification Search
None
See application file for complete search history.

(56) References Cited

U.S. PATENT DOCUMENTS

| | | |
|---|---|---|
| 3,870,795 A | 3/1975 | Miller et al. |
| 4,708,808 A | 11/1987 | Rossmoore |
| 5,312,827 A | 5/1994 | Bayer et al. |
| 5,364,649 A | 11/1994 | Rossmoore et al. |
| 2010/0078393 A1 | 4/2010 | Yin |
| 2010/0093736 A1 | 4/2010 | Coburn et al. |
| 2010/0286096 A1 | 11/2010 | Yin et al. |
| 2011/0041387 A1* | 2/2011 | Green ............... A01N 33/08 44/314 |
| 2011/0046140 A1* | 2/2011 | Brutto ............... A01N 33/08 514/241 |

FOREIGN PATENT DOCUMENTS

EP 0435439 A2 7/1991

OTHER PUBLICATIONS

U.S. Appl. No. 14/287,504, filed May 2015, Annis et al.*
Shmunes, et al., "Allergic contact dermatitis to dimethoxane in a spin finish", Contact Dermatitis, 1980, pp. 421-424, vol. 6.

* cited by examiner

*Primary Examiner* — Svetlana M Ivanova
(74) *Attorney, Agent, or Firm* — Tifani M. Edwards

(57) ABSTRACT

Provided is a biocidal composition comprising 2,6-dimethyl-m-dioxane-4-ol acetate and an isothiazolinone biocidal compound. The composition is useful for controlling microorganisms in aqueous or water containing systems.

5 Claims, No Drawings

BIOCIDAL COMPOSITION OF 2,6-DIMETHYL-M-DIOXANE-4-OL ACETATE AND METHODS OF USE

FIELD OF THE INVENTION

The invention relates to biocidal compositions and methods of their use for the control of microorganisms in aqueous and water containing systems.

BACKGROUND OF THE INVENTION

Isothiazolinone-based biocides are used extensively for protection of water-containing systems such as: paints and coatings, adhesives, household and industrial cleaners, detergents, dish detergents, mineral slurries and polymer emulsions. Formaldehyde releasing biocides have also been extensively used, however, recent public concerns and environmental regulations concerning formaldehyde have begun to limit the use of formaldehyde-releasers as antimicrobial agents. Thus, the isothiazolinone biocides, which are non-formaldehyde releasers, have become increasingly attractive alternatives.

Isothiazolinones, however, also suffer from limitations, such as gaps in efficacy against certain microorganisms and possible potential for skin sensitization. It is desirable, therefore, to develop new formulations based on the existing widely used isothiazolinones but that also address isothiazolinones' limitations. It also desirable that such formulations not be based on formaldehyde releasers.

BRIEF SUMMARY OF THE INVENTION

In one aspect, the invention provides biocidal compositions. The compositions are useful for controlling microorganisms in aqueous or water containing systems. The present invention comprises a composition comprising:
  2,6-dimethyl-m-dioxane-4-ol acetate; and
  2-methyl-3-isothiazolinone
wherein the weight ratio of 2,6-dimethyl-m-dioxane-4-ol acetate to 2-methyl-3-isothiazolinone is between about 145:1 and about 2:1. In a second aspect, the invention provides a method for controlling microorganisms in aqueous or water containing systems. The method comprises treating the system with a biocidal composition as described herein.

DETAILED DESCRIPTION OF THE INVENTION

As noted above, the invention provides biocidal compositions and methods of using them in the control of microorganisms. The compositions comprise 2,6-dimethyl-m-dioxane-4-ol acetate (dimethoxane) together with an isothiazolinone biocidal compound. It has surprisingly been discovered that the combination of dimethoxane and an isothiazolinone are synergistic when used for microorganism control in aqueous or water containing media. That is, the combined materials result in improved biocidal properties than would otherwise be expected based on their individual performance at the particular use-concentration. The observed synergy permits reduced amounts of the materials to be used to achieve acceptable biocidal properties, thus potentially reducing environmental impact and materials cost. Reducing the amount of isothiazolinone is also advantages because of the possible potential for skin sensitization with such compounds.

In addition to exhibiting synergy, the compositions of the invention are also effective for controlling a broader spectrum of microorganism types than would be possible with isothiazolinones alone, including the control of fungi (isothiazolinones such as BIT have limited antifungal efficacy), control of algae, and control of otherwise isothiazolinone-resistant microorganisms. Further, because neither the dimethoxane nor the isothiazolinone compound is a formaldehyde releaser, the compositions can be prepared and used in formaldehyde free form, which is especially advantageous where use of formaldehyde is undesirable.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation against re-growth.

Preferred isothiazolinone compounds for use in the compositions of the invention have the following formula I:

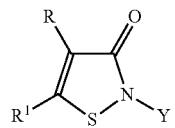

wherein R and $R^1$ are independently hydrogen, halogen or $C_1$-$C_4$ alkyl, or R and $R^1$ together with the carbons to which they are attached from a $C_4$-$C_7$ cycloalkyl ring or an aryl group; and Y is H, $C_1$-$C_{12}$ alkyl, $C_3$-$C_7$ cycloalkyl, aryl or aralkyl.

Also preferred are formula I compounds in which R is H, or Cl. Further preferred are compounds in which $R^1$ is H or Cl. Further preferred are compounds in which R and $R^1$, together with the carbons to which they are attached, form phenyl or cyclopentyl.

Additionally preferred are compounds of formula I in which Y is H, $CH_3$, $CH_2CH_3$, or n-octyl.

Particularly preferred isothiazolinones are 5-chloro-2-methyl-3-isothiazolinone; 2-methyl-3-isothiazolinone; 2-ethyl-3-isothiazolinone; 5-chloro-2-ethyl-3-isothiazolinone; 4,5-dichloro-2-methyl-3-isothiazolinone; 2-n-octyl-3-isothiazolinone; 4,5-dichloro-2-n-octyl-3-isothiazolinone; 1,2-benzisothiazol-3-one; 2-methyl-4,5-trimethylene-4-isothiazolin-3-one; and mixtures of two or more thereof. Especially preferred are 1,2-benzisothiazol-3-one (BIT), 2-methyl-3-isothiazolinone (MIT), and mixtures of 5-chloro-2-methyl-3-isothiazolinone/2-methyl-3-isothiazolinone.

Of course, more than one isothiazolinone compound can be combined for use in the present invention; in such cases, ratios and concentrations are calculated using the total weight of all isothiazolinone compounds present. As noted, a particularly preferred combination is 5-chloro-2-methyl-3-isothiazolinone/2-methyl-3-isothiazolinone.

Preferably, the dimethoxane:isothiazolinone weight ratio in the compositions of the invention is between about 2000:1 and about 1:1000, more preferably between about 1500:1 and about 1:500, even more preferably between about 1500:1 and about 1:100. In further preferred embodiments, the weight ratio is between about 1400:1 and about 1:10 or is between about 1400:1 and about 1:3. In additional embodiments, the weight ratio is between about 1000:1 and about 1:3, between about 500:1 and about 1:3, between about 100:1 and about 1:3, or between about 50:1 and about 1:3.

In further embodiments, when the isothiazolinone biocidal compound is 1,2-benzisothiazol-3-one, it is further preferred that the weight ratio of dimethoxane to the 1,2-benzisothiazol-3-one is between about 50:1 and about 1:4.

In still further preferred embodiments, when the isothiazolinone biocidal compound is a mixture of 5-chloro-2-methyl-3-isothiazolinone and 2-methyl-3-isothiazolinone, it is further preferred that the weight ratio of dimethoxane to the mixture is between about 900:1 and about 10:1.

In yet further preferred embodiments, when the isothiazolinone biocidal compound is 2-methyl-3-isothiazolinone, the weight ratio of dimethoxane to the 2-methyl-3-isothiazolinone is preferably between about 150:1 and about 2:1.

In another preferred embodiment, the microorganism being treated is algae and the aqueous or water containing system is latex. The biocidal composition for this embodiment preferably comprises: dimethoxane and a mixture of 5-chloro-2-methyl-3-isothiazolinone and 2-methyl-3-isothiazolinone. The weight ratio of the dimethoxane to the mixture of 5-chloro-2-methyl-3-isothiazolinone and 2-methyl-3-isothiazolinone is preferably between about 150:1 and about 30:1.

Isothiazolinones for use in the invention are commercially available or can be readily prepared by those skilled in the art using well known techniques (see e.g., U.S. Pat. No. 5,312,827). Dimethoxane is commercially available. In some embodiments, it is desirable to formulate the isothiazolinone containing compositions of the invention in solutions containing water or organic solvent or mixtures thereof together with nitrate or nitrite stabilizers to prevent decomposition of the isothiazolinone (see U.S. Pat. No. 3,870,795). A preferred stabilizer is magnesium nitrate.

The compositions of the invention are useful at controlling microorganism growth in a variety of aqueous and water containing systems. Examples of such systems include, but are not limited to, paints and coatings, latexes, adhesives, inks, pigment dispersions, household and industrial cleaners, detergents, dish detergents, mineral slurries polymer emulsions, metalworking fluids, construction products, personal care products, textile fluids such as spin finishes, industrial process water (e.g. oilfield water, pulp and paper water, cooling water), oilfield functional fluids such as drilling muds and fracturing fluids, and fuels.

A person of ordinary skill in the art can readily determine, without undue experimentation, the concentration of the composition that should be used in any particular application. By way of illustration, a suitable actives concentration (total for both dimethoxane and the isothiazolinone) is between about 5000 and about 100 ppm by weight, based on the total weight of the aqueous or water containing system. By way of more specific illustration, for a composition comprising dimethoxane and BIT, the active concentration is preferably between about 2500 ppm and about 350 ppm. For the dimethoxane/CMIT/MIT combination, the concentration is preferably between about 1800 ppm and about 300 ppm.

The components of the composition can be added to the aqueous or water containing system separately, or pre-blended prior to addition. A person of ordinary skill in the art can readily determine the appropriate method of addition. The composition can be used in the system with other additives such as, but not limited to, surfactants, ionic/nonionic polymers and scale, corrosion inhibitors, oxygen scavengers, and/or additional biocides.

The following examples are illustrative of the invention but are not intended to limit its scope.

EXAMPLES

General.

Experimental Setup: In the following examples, tests are conducted in a 96-deep well block format using a total sample volume of 600 µl for all evaluations. In these samples, no more than 10% of the total volume consists of the biocide and organism solution and all non-matrix additions are normalized for all samples. Each experimental 96-well block contains biocide-treated samples and control samples which lack biocide.

Biocides:

2,6-Dimethyl-m-dioxan-4-ol acetate (dimethoxane) is used as BIOBAN™ DXN, 87% active, available from The Dow Chemical Company.

1,2-benzisothiazol-3-one (BIT) is used as CAN-GUARD™ ULTRA BIT 20 LE, 20% active, available from The Dow Chemical Company.

2-Methyl-3-isothiazolinone (MIT) is used as Kordek™ 50C Industrial Microbicide.

5-Chloro-2-methyl-4-isothiazolin-3-one/2-methyl-4-isothiazolin-3-one (CMIT/MIT) is used as CANGUARD™ CM1p5, 1.11% active CMIT; 0.39% active MIT, available from The Dow Chemical Company.

Microorganisms: Twenty-four hour tryptic soy broth cultures are combined in equal parts for formulation inoculation at a final concentration of $5 \times 10^6$ CFU/ml. Organisms are added to each sample of the 96-well block and mixed until homogenous. Additionally, bacterial challenges of the industrial or household product occur on days 2, 7, and 14 of the 28-day test period.

Enumeration of Viable Organisms: Sample aliquots are removed, at predetermined time points, for the enumeration of surviving microorganisms. Numerical values in the data tables listed below represent the $\log_{10}$ viable microorganisms recovered from individual samples at specific time points and biocide concentrations post microorganism addition. Biocide concentrations resulting in a ≥4 $\log_{10}$ kill of microorganisms, as compared to the preservative-free control, were deemed a significant reduction of viable organisms and were subsequently used for calculating synergy index values.

Synergy Calculations: The reported synergy indexes are measured and calculated using the formula described below. In this approach, a synergy index of 1 indicates additivity. If the index is less than 1, synergy has occurred, while a synergy index greater than 1 indicates antagonism.

$$\text{Synergy index} = C_A/C_a + C_B/C_b$$

$C_a$=minimal concentration of antimicrobial A, alone, producing a 4 $\log_{10}$ microbial kill $C_b$=minimal concentration of antimicrobial B, alone, producing a 4 $\log_{10}$ microbial kill $C_A$ and $C_B$=the concentrations of antimicrobials A and B, in combination, producing a 4 $\log_{10}$ microbial kill.

Example 1

Evaluation of dimethoxane/1,2-benzisothiazol-3-one (BIT)
A) Detergent Matrix

The antimicrobial profiles dimethoxane, 1,2-benzisothiazol-3-one (BIT), and combinations of dimethoxane/BIT are evaluated in a commercial liquid laundry detergent formulation (pH 8.0). The detergent formulation is determined to be free of microbial contamination prior to initiation of preservative efficacy evaluations.

B) Paint Matrix

The antimicrobial profiles of dimethoxane, BIT, and combinations of dimethoxane/BIT are evaluated in a commercial (interior eggshell) water-based latex paint formulation (pH 7.4). The paint formulation is determined to be free of microbial contamination prior to initiation of preservative efficacy evaluations.

Organisms for this example: *Pseudomonas aeruginosa* (ATCC #15442), *Pseudomonas aeruginosa* (ATCC #10145), *Enterobacter aerogenes* (ATCC #13048), *Escherichia coli* (ATCC #11229), *Klebsiella pneumoniae* (ATCC #8308), *Staphylococcus aureus* (ATCC #6538), *Salmonella choleraesuis* (ATCC #10708).

Results for dimethoxane/BIT in detergent are provided in Tables 1 and 2.

TABLE 1

DAY 20 viable microorganism enumeration (post 4$^{th}$ microbial challenge)

| DMX (ppm a.i.) | BIT (ppm a.i.) | | | | | | | | DMX alone | BIT alone score | ppm |
|---|---|---|---|---|---|---|---|---|---|---|---|
| | 300 | 200 | 133 | 89 | 59 | 40 | 26 | 18 | DMX | score | ppm |
| 1740 | 0.0 | 0.0 | 0.0 | 0.0 | 0.0 | 0.0 | 0.0 | 0.0 | 0.0 | 1.0 | 300 |
| 1160 | 0.0 | 0.0 | 0.0 | 0.0 | 0.0 | 0.0 | 0.0 | 0.0 | 0.0 | 1.0 | 200 |
| 773 | 0.0 | 0.0 | 0.0 | 0.0 | 0.0 | 0.0 | 0.0 | 0.0 | 4.0 | 0.0 | 133 |
| 516 | 0.0 | 0.0 | 0.0 | 0.0 | 0.0 | 0.0 | 0.0 | 0.0 | 6.0 | 0.0 | 89 |
| 344 | 0.0 | 0.0 | 1.0 | 0.0 | 0.0 | 0.0 | 0.0 | 0.0 | 5.0 | 0.0 | 59 |
| 229 | 0.0 | 0.0 | 0.0 | 0.0 | 0.0 | 0.0 | 2.0 | 7.0 | 6.0 | 3.0 | 40 |
| 153 | 0.0 | 0.0 | 0.0 | 0.0 | 0.0 | 1.0 | 4.0 | 6.0 | 6.0 | 7.0 | 26 |
| 102 | 0.0 | 0.0 | 0.0 | 0.0 | 0.0 | 2.0 | 3.0 | 7.0 | 6.0 | 6.0 | 18 |
| Controls | 6.4 | 6.4 | 6.4 | 6.4 | 6.4 | 6.4 | 6.4 | 6.4 | 6.4 | 6.4 | 0 |

DMX = Dimethoxane; a.i. = active ingredient (i.e., actives concentration)

TABLE 2

Synergy index calculations

| Time | DMX:BIT ratio | DMX alone (ppm) | BIT alone (ppm) | DMX in combination (ppm) | BIT in combination (ppm) | Synergy Index |
|---|---|---|---|---|---|---|
| Day 20 | 4:1 | 1160 | 59 | 153 | 40 | .810 |
| Day 20 | 6:1 | 1160 | 59 | 229 | 40 | .875 |
| Day 20 | 9:1 | 1160 | 59 | 229 | 26 | .638 |
| Day 20 | 13:1 | 1160 | 59 | 344 | 26 | .738 |
| Day 20 | 20:1 | 1160 | 59 | 516 | 26 | .886 |
| Day 20 | 29:1 | 1160 | 59 | 516 | 18 | .750 |
| Day 20 | 43:1 | 1160 | 59 | 773 | 18 | .971 |

*Biocide concentrations represented as ppm active dimethoxane or BIT

DMX = Dimethoxane

Dimethoxane, when used alone, requires 1160 ppm (active concentration) to achieve a ≥4 log$_{10}$ microbial kill following four bacterial challenges. BIT by itself requires 59 ppm (active concentration) to achieve a ≥4 log$_{10}$ microbial kill under the same testing conditions. Use of various concentration ratios of BIT and dimethoxane in combination result in an equivalent log$_{10}$ reduction in viable microorganisms under the same testing conditions indicating a synergistic combination of biocide actives.

Results for dimethoxane/BIT in paint are shown in Tables 3 and 4.

TABLE 3

DAY 15 viable microorganism enumeration (post 4$^{th}$ microbial challenge)

| DMX (ppm a.i.) | BIT (ppm a.i.) | | | | | | | | DMX alone | BIT alone score | ppm |
|---|---|---|---|---|---|---|---|---|---|---|---|
| | 500 | 333 | 222 | 148 | 99 | 66 | 44 | 29 | alone | score | ppm |
| 1740 | 0 | 0 | 0 | 0 | 0 | 0 | 0 | 0 | 0 | 5 | 500 |
| 1160 | 0 | 0 | 0 | 0 | 1 | 2 | 3 | 2 | 3 | 8 | 333 |
| 773 | 0 | 1 | 4 | 2 | 2 | 3 | 3 | 3 | 7 | 8 | 222 |
| 516 | 0 | 0 | 0 | 4 | 3 | 4 | 4 | 4 | 8 | 7 | 148 |
| 344 | 0 | 0 | 4 | 4 | 8 | 6 | 5 | 8 | 7 | 7 | 99 |
| 229 | 0 | 0 | 5 | 5 | 8 | 8 | 7 | 8 | 7 | 6 | 66 |
| 153 | 0 | 0 | 4 | 8 | 7 | 8 | 7 | 7 | 8 | 7 | 44 |
| 102 | 0 | 0 | 5 | 6 | 7 | 8 | 8 | 8 | 7 | 8 | 29 |
| Controls | 7 | 7 | 7 | 7 | 7 | 7 | 7 | 7 | 7 | 7 | 0 |

DMX = Dimethoxane

TABLE 4

Synergy index calculations

| Time | DMX:BIT ratio | DMX alone (ppm) | BIT alone (ppm) | DMX in combination (ppm) | BIT in combination (ppm) | Synergy Index |
|---|---|---|---|---|---|---|
| Day 15 | 1:1 | 1160 | >500 | 344 | 333 | <0.963 |
| Day 15 | 1:1.5 | 1160 | >500 | 229 | 333 | <0.863 |
| Day 15 | 1:2 | 1160 | >500 | 153 | 333 | <0.798 |
| Day 15 | 1:3.3 | 1160 | >500 | 102 | 333 | <0.754 |
| Day 15 | 27:1 | 1160 | >500 | 773 | 29 | <0.724 |
| Day 15 | 18:1 | 1160 | >500 | 773 | 44 | <0.754 |
| Day 15 | 12:1 | 1160 | >500 | 773 | 66 | <0.798 |
| Day 15 | 8:1 | 1160 | >500 | 773 | 99 | <0.864 |
| Day 15 | 5:1 | 1160 | >500 | 516 | 99 | <0.643 |
| Day 15 | 2:1 | 1160 | >500 | 516 | 222 | <0.889 |

*Biocide concentrations represented as ppm active dimethoxane or BIT
DMX = Dimethoxane Dimethoxane, when used alone, requires 1160 ppm to achieve a ≥4 $\log_{10}$ microbial kill following four bacterial challenges. BIT by itself requires greater than 500 ppm to achieve a ≥4 $\log_{10}$ microbial kill under the same testing conditions. Use of various concentration ratios of BIT and dimethoxane results in an equivalent $\log_{10}$ reduction in viable microorganisms under the same testing conditions indicating a synergistic combination of biocide actives.

Example 2

Evaluation of dimethoxane/2-methyl-3-isothiazolinone (MIT)

The antimicrobial profiles of 2,6-dimethyl-m-dioxan-4-ol acetate (dimethoxane), 2-methyl-3-isothiazolinone (MIT), and combinations of dimethoxane/MIT are evaluated in a commercial liquid laundry detergent formulation (pH 8.0). The detergent formulation is determined to be free of microbial contamination prior to initiation of preservative efficacy evaluations.

Organisms for this example: *Pseudomonas aeruginosa* (ATCC #15442), *Pseudomonas aeruginosa* (ATCC #10145), *Enterobacter gergoviae* (ATCC #33028), *Escherichia coli* (ATCC #11229), *Pseudomonas putida* (ATCC #49128), *Staphylococcus aureus* (ATCC #6538).

Results for (dimethoxane and MIT and combinations are provided in Tables 5 and 6.

TABLE 5

DAY 20 viable microorganism enumeration (post 4th microbial challenge)

| DMX (ppm) | MIT (ppm a.i.) | | | | | | | | DMX Alone | MIT Alone score | ppm |
|---|---|---|---|---|---|---|---|---|---|---|---|
| | 50 | 33 | 22 | 15 | 10 | 7 | 4 | 3 | | | |
| 1305 | 0.0 | 0.0 | 0.0 | 0.0 | 0.0 | 0.0 | 0.0 | 0.0 | 0.0 | 3.0 | 50 |
| 870 | 0.0 | 0.0 | 0.0 | 0.0 | 0.0 | 0.0 | 0.0 | 1.0 | 1.0 | 8.0 | 33 |
| 580 | 0.0 | 0.0 | 0.0 | 0.0 | 0.0 | 0.0 | 2.0 | 3.0 | 3.0 | 8.0 | 22 |
| 386 | 0.0 | 0.0 | 2.0 | 4.0 | 8.0 | 8.0 | 8.0 | 8.0 | 4.0 | 8.0 | 15 |
| 257 | 0.0 | 0.0 | 2.0 | 6.0 | 8.0 | 8.0 | 8.0 | 8.0 | 5.0 | 8.0 | 10 |
| 172 | 0.0 | 2.0 | 8.0 | 8.0 | 8.0 | 8.0 | 8.0 | 8.0 | 8.0 | 8.0 | 7 |
| 115 | 0.0 | 1.0 | 8.0 | 8.0 | 8.0 | 8.0 | 8.0 | 8.0 | 8.0 | 8.0 | 4 |
| 77 | 0.0 | 2.0 | 8.0 | 8.0 | 8.0 | 8.0 | 8.0 | 8.0 | 8.0 | 8.0 | 3 |
| Controls | 8.0 | 8.0 | 8.0 | 8.0 | 8.0 | 8.0 | 8.0 | 8.0 | 8.0 | 8.0 | 0 |

DMX = Dimethoxane

TABLE 6

Synergy Index Calculation

| Time | DMX:MIT Ratio | DMX Alone | MIT Alone (ppm) | DMX in Combination (ppm) | MIT in Combination (ppm) | Synergy Index |
|---|---|---|---|---|---|---|
| Day 20 | 2:1 | 870 | >50 | 77 | 33 | <0.75 |
| Day 20 | 3.5:1 | 870 | >50 | 115 | 33 | <0.79 |
| Day 20 | 5:1 | 870 | >50 | 172 | 33 | <0.86 |
| Day 20 | 8:1 | 870 | >50 | 257 | 33 | <0.96 |
| Day 20 | 12:1 | 870 | >50 | 257 | 22 | <0.74 |
| Day 20 | 18:1 | 870 | >50 | 386 | 22 | <0.88 |
| Day 20 | 26:1 | 870 | >50 | 386 | 15 | <0.74 |
| Day 20 | 39:1 | 870 | >50 | 580 | 15 | <0.97 |
| Day 20 | 58:1 | 870 | >50 | 580 | 10 | <0.87 |
| Day 20 | 83:1 | 870 | >50 | 580 | 7 | <0.81 |
| Day 20 | 145:1 | 870 | >50 | 580 | 4 | <0.75 |

DMX = Dimethoxane

Example 3

Dimethoxane with 5-chloro-2-methyl-3-isothiazolinone/2-methyl-3-isothiazolinone (CMIT/MIT)

The antimicrobial profiles of 2,6-dimethyl-m-dioxan-4-ol acetate (dimethoxane), 5-chloro-2-methyl-4-isothiazolin-3-one/2-methyl-4-isothiazolin-3-one (CMIT/MIT) and combinations of dimethoxane/CMIT/MIT are evaluated in a commercial (interior eggshell) water-based latex paint formulation (pH 7.4). The paint formulation is determined to be free of microbial contamination prior to initiation of preservative efficacy evaluations.

Organisms for this example: *Pseudomonas aeruginosa* (ATCC #15442), *Pseudomonas aeruginosa* (ATCC #10145), *Enterobacter aerogenes* (ATCC #13048), *Escherichia coli* (ATCC #11229), *Klebsiella pneumoniae* (ATCC #8308), *Staphylococcus aureus* (ATCC #6538), *Salmonella choleraesuis* (ATCC #10708).

Results for dimethoxane/CMIT/MIT and combinations are provided in Tables 7 and 8.

TABLE 7

DAY 20 viable microorganism enumeration (post 4th microbial challenge)

| DMX (ppm a.i.) | CMIT/MIT (ppm a.i.) | | | | | | | DMX alone | CMIT/MIT alone score | ppm |
|---|---|---|---|---|---|---|---|---|---|---|
| | 15 | 10 | 6.7 | 4.4 | 3 | 2 | 1.3 | 0.9 | | | |
| 1740 | 0 | 0 | 0 | 0 | 0 | 0 | 0 | 2 | 2 | 2 | 15 |
| 1160 | 0 | 0 | 0 | 0 | 0 | 0 | 0 | 5 | 6 | 5 | 10 |
| 773 | 0 | 0 | 0 | 0 | 0 | 7 | 6 | 8 | 8 | 8 | 6.7 |
| 516 | 0 | 0 | 0 | 7 | 8 | 8 | 8 | 8 | 8 | 8 | 4.4 |
| 344 | 0 | 0 | 0 | 8 | 8 | 8 | 8 | 8 | 7 | 8 | 3 |
| 229 | 0 | 0 | 8 | 8 | 7 | 7 | 8 | 8 | 7 | 8 | 2 |
| 153 | 0 | 0 | 8 | 8 | 8 | 8 | 8 | 8 | 8 | 8 | 1.3 |
| 102 | 0 | 0 | 8 | 8 | 8 | 8 | 7 | 8 | 8 | 8 | 0.9 |
| Controls | 8 | 8 | 8 | 8 | 8 | 8 | 8 | 8 | 8 | 8 | 0 |

DMX = Dimethoxane

TABLE 8

Synergy index calculations

| Time | DMX:CMIT/MIT ratio | DMX alone (ppm) | CMIT/MIT alone (ppm) | DMX in combination (ppm) | CMIT/MIT in combination (ppm) | Synergy Index |
|---|---|---|---|---|---|---|
| Day 20 | 10:1 | 1740 | 15 | 102 | 10 | 0.762 |
| Day 20 | 15:1 | 1740 | 15 | 153 | 10 | 0.755 |
| Day 20 | 23:1 | 1740 | 15 | 229 | 10 | 0.799 |
| Day 20 | 51:1 | 1740 | 15 | 344 | 6.7 | 0.645 |
| Day 20 | 115:1 | 1740 | 15 | 773 | 6.7 | 0.891 |
| Day 20 | 176:1 | 1740 | 15 | 773 | 4.4 | 0.737 |
| Day 20 | 258:1 | 1740 | 15 | 773 | 3 | 0.644 |
| Day 20 | 263:1 | 1740 | 15 | 1160 | 4.4 | 0.960 |
| Day 20 | 387:1 | 1740 | 15 | 1160 | 3 | 0.867 |
| Day 20 | 580:1 | 1740 | 15 | 1160 | 2 | 0.800 |
| Day 20 | 892:1 | 1740 | 15 | 1160 | 1.3 | 0.754 |

*Biocide concentrations as ppm active dimethoxane or CMIT/MIT
DMX = Dimethoxane

Dimethoxane, when used alone, requires 1740 ppm to achieve a $\geq 4$ $\log_{10}$ microbial kill following four bacterial challenges. CMIT/MIT by itself requires 15 ppm to achieve a $\geq 4$ $\log_{10}$ microbial kill under the same testing conditions. Use of various concentration ratios of CMIT/MIT and dimethoxane results in an equivalent $\log_{10}$ reduction in viable microorganisms under the same testing conditions indicating a synergistic combination of biocide actives.

Example 4

Evaluation of dimethoxane and CMIT/MIT against Algae in PVA Latex

Procedure. In this example, a viscous PVA (poly vinyl acetate) latex diluted with water at 5 to 1 ratio is used for algal efficacy testing. This diluted latex is treated with CMIT/MIT and dimethoxane at concentrations as indicated in Table 9. Each sample is mixed well by hand and vortex for 2 minutes. 5 mL portions of each sample are then placed in a six-well plate and inoculated with 500 μL of $1 \times 10^6$ cfu/mL wild strain of green algae isolated from contaminated PVA latex.

The plates are incubated at room temp (25° C.-26° C.) under cyclic exposure to light (OTT-Lite model # OTL4012P, 40 Watt, 26 KLumen) and dark phases, for a period of three weeks. Biocidal efficacy results are shown in Table 9.

TABLE 9

Challenge Testing of PVA latex against wild strain of Green Algae

| CMIT/MIT ppm | Dimethoxane ppm | Dimethoxane:CMIT/MIT ratio | % algal growth Sample A | % algal growth Sample B |
|---|---|---|---|---|
| 15 | 500 | 33.3:1 | 20% | 20% |
| 15 | 1000 | 66.6:1 | 3% | 3% |
| 15 | 1500 | 100:1 | no growth | no growth |
| 15 | 2000 | 133.3:1 | no growth | no growth |
| 15 | 0 | — | 100% | 100% |
| 0 | 2000 | — | 15% | 15% |
| 0 | 0 | — | 100% | 100% |

The data shows the effectiveness of the dimethoxane/CMIT/MIT combination of the invention compared to the dimethoxane and CMIT/MIT individually.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A composition comprising:
   2,6-dimethyl-m-dioxane-4-ol acetate; and
   2-methyl-3-isothiazolinone
   wherein the weight ratio of 2,6-dimethyl-m-dioxane-4-ol acetate to 2-methyl-3-isothiazolinone is between about 145:1 and about 2:1.

2. A composition according to claim 1 further comprising one or more surfactants, ionic/nonionic polymers and scale, corrosion inhibitors, oxygen scavengers or additional biocides.

3. A method for controlling microorganisms in an aqueous or water containing system, the method comprising treating the system with a composition according to claim 1.

4. A method according to claim 3 wherein the aqueous or water containing system is selected from the group consisting of paints and coatings; latexes; adhesives; inks; pigment dispersions; household and industrial cleaners; detergents; mineral slurries; polymer emulsions; metalworking fluids; construction products; personal care products; textile fluids; industrial process water; oilfield functional fluids and fuels.

5. A method according to claim 4 wherein the aqueous or water containing system is selected from a group consisting of paints and detergents.

* * * * *